United States Patent
Crocetti

(10) Patent No.: US 8,356,602 B2
(45) Date of Patent: Jan. 22, 2013

(54) DEVICES FOR TREATING OBSTRUCTIVE SLEEP APNEA AND/OR SNORING

(76) Inventor: Joseph Crocetti, Jenkintown, PA (US)

(*) Notice: Subject to any disclaimer, the term of this patent is extended or adjusted under 35 U.S.C. 154(b) by 911 days.

(21) Appl. No.: 11/741,973

(22) Filed: Apr. 30, 2007

(65) Prior Publication Data

US 2007/0256695 A1 Nov. 8, 2007

Related U.S. Application Data

(60) Provisional application No. 60/797,312, filed on May 3, 2006.

(51) Int. Cl.
*A61F 5/56* (2006.01)
*A61F 5/30* (2006.01)

(52) U.S. Cl. ..................... 128/848; 128/112.1

(58) Field of Classification Search ............ 128/846, 128/848, 112.1, 100.1, 106.1, 845
See application file for complete search history.

(56) References Cited

U.S. PATENT DOCUMENTS

| | | | |
|---|---|---|---|
| 876,491 A | 1/1908 | Rohwer | |
| 898,379 A | 9/1908 | Liebhardt | |
| 2,304,235 A | 12/1942 | Boots | |
| 3,485,241 A | 12/1969 | Polley | |
| 4,905,993 A * | 3/1990 | Barone | 482/106 |
| 4,989,591 A * | 2/1991 | Anders, Jr. | 606/240 |
| 5,199,124 A * | 4/1993 | Klemis | 5/630 |
| 5,357,981 A | 10/1994 | Eilam | |
| 6,357,444 B1 * | 3/2002 | Parker | 128/848 |
| 6,926,008 B1 | 8/2005 | Levitt | |
| 2001/0015208 A1 * | 8/2001 | Konishi | 128/848 |
| 2005/0087194 A1 * | 4/2005 | Scott | 128/846 |

* cited by examiner

*Primary Examiner* — Loan Thanh
*Assistant Examiner* — Tarla Patel
(74) *Attorney, Agent, or Firm* — Caesar, Rivise, Bernstein, Cohen & Pokotilow, Ltd.

(57) ABSTRACT

A garment for the treatment of sleep apnea and/or snoring includes a member for attachment to an individual afflicted with sleep apnea and an elongate, position control member at the rear of the garment and extending outwardly therefrom. The elongate member is a continuous member having transversely spaced-apart side surfaces, and the side surfaces are joined to an outer wall of the position control member at elongate side edges. The side surfaces and/or side edges are located to engage a mattress or other sleeping surface when an individual wearing the garment is sleeping in a lateral position to aid in supporting the individual in a lateral position.

9 Claims, 3 Drawing Sheets

DEVICES FOR TREATING OBSTRUCTIVE SLEEP APNEA AND/OR SNORING

RELATED APPLICATIONS

This utility application claims the benefit under 35 U.S.C. §119(e) of Provisional Application Ser. No. 60/797,312 filed on May 3, 2006 entitled DEVICES FOR TREATING OBSTRUCTIVE SLEEP APNEA AND/OR SNORING and whose entire disclosure is incorporated by reference herein.

BACKGROUND OF THE INVENTION

1. Field of Invention

This invention relates generally to a device for treating obstructive sleep apnea, and more specifically, to a garment employed for treating obstructive sleep apnea.

2. Description of Related Art

Numerous garments have been proposed for treating obstructive sleep apnea. It should be noted that obstructive sleep apnea can be either positional or non-positional. Positional sleep apnea manifests itself when an individual is sleeping in a supine position. Although non-positional sleep apnea tends to manifest itself in all body positions, it still tends to be most severe when the individual is in a supine position. Also, as is well known, the effective treatment of sleep apnea often tends to reduce or minimize snoring.

A number of prior art garments for dealing with sleep apnea employ a pad, ball, or other member extending outwardly from the patient's back, generally in the center region thereof. If a person with sleep apnea rolls onto his/her back while sleeping, a position which may cause the partial or complete closure of the individual's airway, the raised member will provide the desired degree of discomfort either to wake up the individual or to force the individual back into a prone or lateral position, i.e., a position facing downward or on his/her side. Representative garments that provide the above-stated function are disclosed in U.S. Pat. Nos. 876,491; 898,379; 2,304,235; 3,485,241; 5,357,981 and 6,357,444. In addition to the above enumerated patents, there are several other patents that disclose similar features. However, these prior art devices are not well designed to assist in maintaining a person in a lateral position while sleeping.

Another approach to deal with the problem of obstructive sleep apnea, and in particular to aid in preventing a person from sleeping in a supine position, is to provide a garment with spaced-apart abutments, each being designed to maintain an individual on a respective lateral side while sleeping. However, it is believed that if a sleeping individual does roll onto his back (i.e., into a supine position) this latter garment may not create sufficient discomfort to either wake up the individual or cause the individual to roll back into either a prone or lateral position. A representative device employing space-apart abutments is disclosed in U.S. Pat. No. 6,926,008.

Applicant believes that an improved garment for treating sleep apnea is needed, which is relatively simple in construction, and has the capability of both assisting in initially maintaining an individual in a comfortable, prone or lateral position while sleeping, and also creating a sufficient degree of discomfort when the individual moves into a supine position, to either wake the individual up or force the individual to move back into a prone or lateral position. It is to such a simplified device that the present invention relates All references cited herein are incorporated herein by reference in their entireties.

BRIEF SUMMARY OF THE INVENTION

A garment for the treatment of sleep apnea includes a member for attachment to an individual afflicted with sleep apnea and an elongate, position control member at the rear of the garment and extending outwardly therefrom. The elongate member is a continuous member having transversely spaced-apart side surfaces, said side surfaces being joined to an outer wall of said member at elongate side edges. The said side surfaces and/or side edges are located to engage a mattress or other sleeping surface when an individual wearing the garment is sleeping in a lateral position.

BRIEF DESCRIPTION OF SEVERAL VIEWS OF THE DRAWINGS

The invention will be described in conjunction with the following drawings in which like reference numerals designate like elements and wherein.

DESCRIPTION OF THE PREFERRED EMBODIMENTS OF THE INVENTION

Reference throughout this application to a "garment" is intended to broadly refer to any member that can be worn or supported on the body of an individual. The garment, therefore, includes such members as belts, shirts, vests, straps, etc. Although the garment in the preferred embodiment of the invention is in the form of a strap or belt member, in accordance with the broadest aspects of the invention it can include any other structure that can be worn or supported on the body of the individual.

Throughout this application, reference to the position or location of surfaces or members, (e.g., rear, upward, lower, side, outer, inner, etc.) refers to the relative orientation/position of such surfaces or members when the garment is being worn by an individual who is in a standing position. It should be noted that the garment of this invention is intended to treat positional sleep apnea and also will reduce the severity of non-positional sleep apnea.

Figure 1:
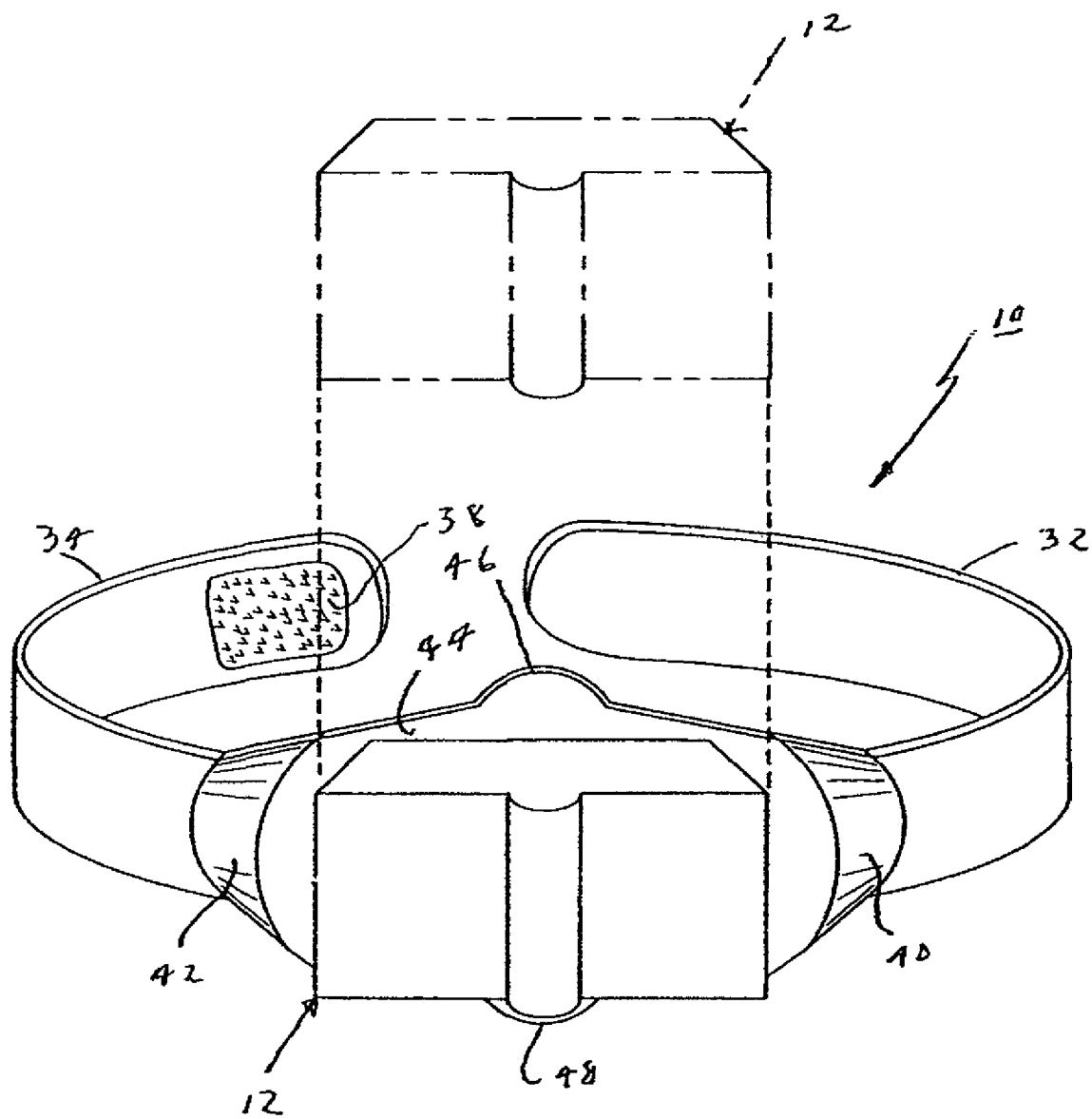
FIG. 1 is an isometric view showing a garment for treating obstructive sleep apnea in accordance with this invention, with the position control member illustrated as a separate element in phantom.
Figure 2:
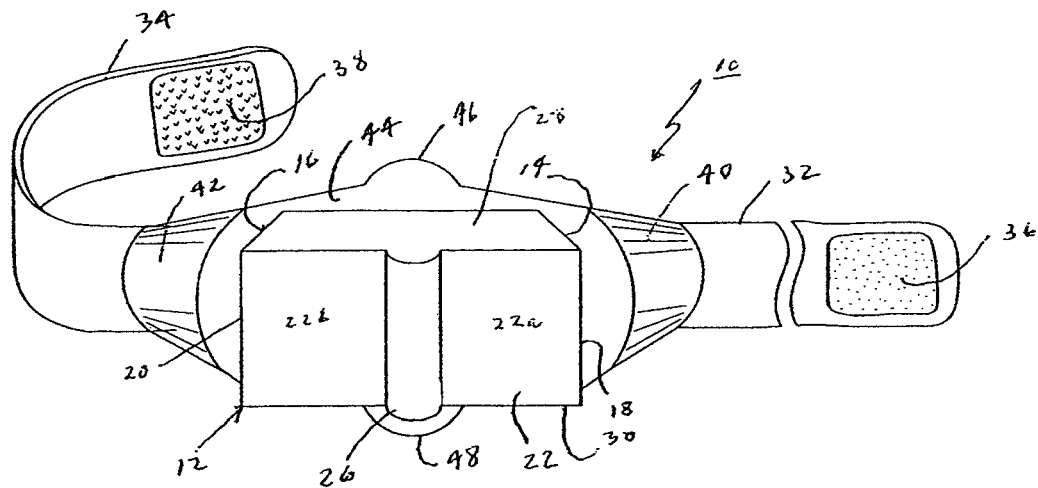
FIG. 2 is a partial isometric view of the device illustrated in FIG. 1, showing additional details of construction.

Referring to FIGS. 1 and 2 a representative garment employing a unique position control member for treating sleep apnea is generally shown at 10. The most unique feature of this garment resides in the unique, elongate, position control member 12. This member 12 can be made of any suitable materials; preferably a material that is compressible, such as a plastic foam (polyurethane, polystyrene, etc.). This unique position control member 12, unlike other devices, has an elongate lateral dimension defined between opposed side surfaces 14 and 16, with the elongate dimension being established to aid in supporting/maintaining an individual while that individual is sleeping in a lateral position. In other words, the respective side surfaces 14 and 16, or at least an outer edge surface 18, 20 of a respective side surface is designed to engage the sleeping surface of a bed while an individual is lying in a lateral position, i.e., lying on his/her side. This engagement aids in maintaining the individual in a lateral position to minimize the likelihood of the individual rolling into a supine position that could completely or partially close off the airway of the individual during the time he or she is sleeping.

Figure 3:
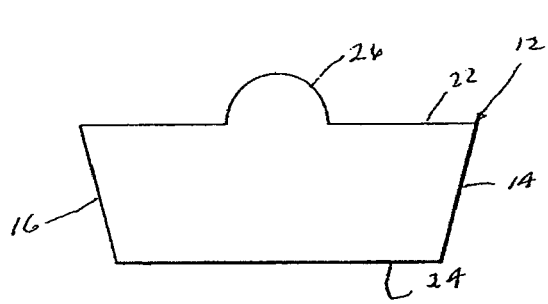
FIG. 3 is a bottom view of the position control member employed as part of the garment for the treatment of sleep apnea, it being understood that the top view has a similar appearance.
Figure 4:
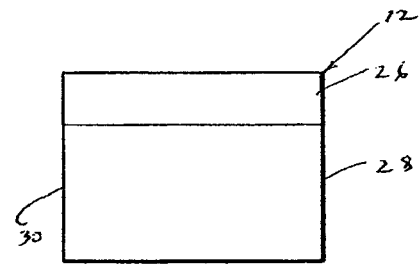
FIG. 4 is a side elevation view of the member illustrated in FIG. 3.
Figure 5:
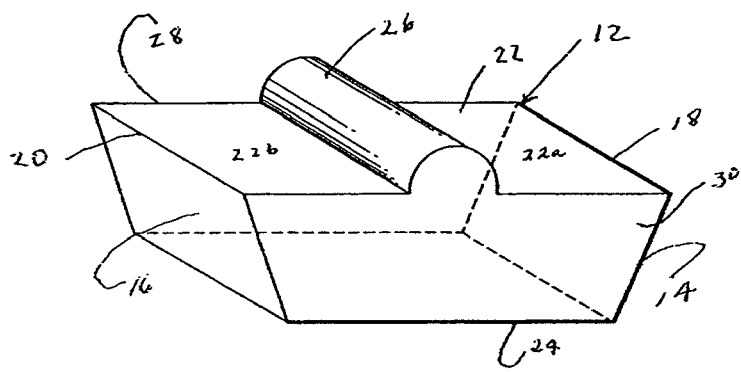
FIG. 5 is an isometric view of the member illustrated in FIG. 3.

As can be seen best in FIGS. 3 and 5, the side surfaces 14 and 16 taper toward each other in an inward direction, from outer surface 22 to inner surface 24 of the position control member 12. Although this is considered to be a preferred structure, thereby permitting the compressible member 12 to engage the mattress or other sleep supporting surface generally along either outer edge 18 or 20 (depending on which side an individual is sleeping), it is within the broad scope of this invention to provide side surfaces or walls 14 and 16 in other orientations, such as normal to the outer and inner surfaces 22 and 24, respectively.

In the most preferred embodiment of this invention, a generally vertically elongate, positioning rib or abutment 26 extends outwardly from outer surface segment 22*a*, 22*b* of the position control member 12, between upper and lower surfaces 28 and 30 of said member. This elongate positioning rib 26, in a preferred construction, is generally hemispherical, is located generally midway between outer edge surfaces 18 and 20 of the position control member 12 and is a unitary part of said member.

It should be noted that, in accordance with the broadest aspects of the invention, the elongate member 12 can be provided as part of the garment 10 in a variety of different ways.

In the illustrated embodiment, the garment 10 is shown in the form of a belt or strap having first strap portions 32, 34 intended to encircle the side and front regions of an individual's torso. The strap portions 32, 34 include cooperating Velcro fastening elements 36, 38 (FIG. 2) adjacent forward edges thereof to maintain the belt in a desired position/orientation about the individual's torso. The rear edges of the strap portions 32, 34, in the illustrative embodiment, are connected to intermediate, elastic sections 40, 42, to enable the strap portions to be stretched about the person's torso prior to interconnecting them through the cooperating Velcro members 40 and 42. This should maintain the garment in a secure manner about the individual's torso. In addition the inclusion of the elastic sections 40, 42 permits inspiratory chest excursion.

Referring to FIGS. 1 and 2, the garment 10 also includes a back panel 44 secured at its opposed lateral edges to the elastic members 40 and 42, and this back panel includes the position control member 12 on (or in) it. As illustrated, the back panel includes enlarged, upper and lower contoured segments 46, 48 for generally engaging the wearers back in the spinal region thereof. These raised contoured segments provide additional stability for the garment 10 and the position control member 12 forming a part thereof.

Figure 6:
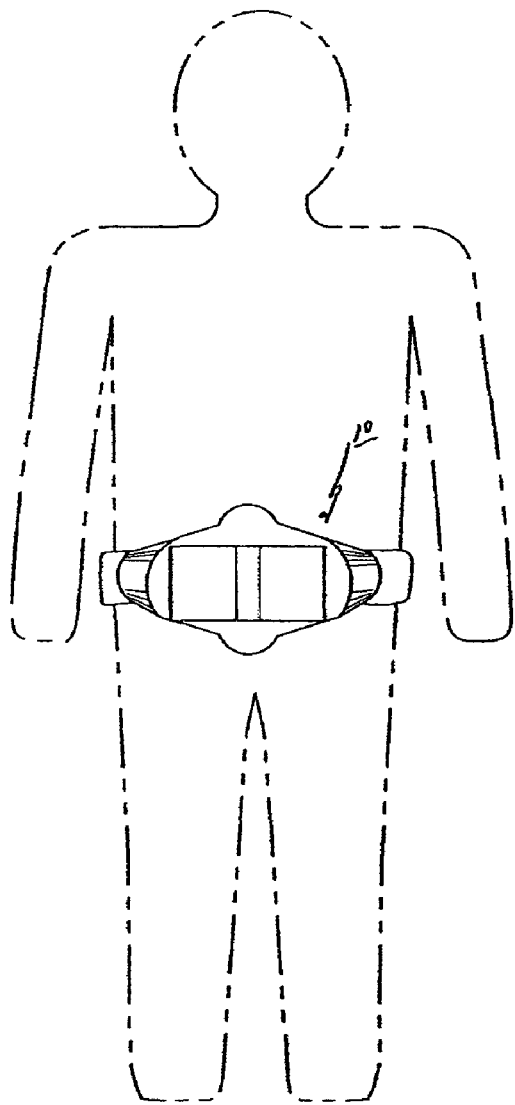
FIG. 6 illustrates the garment shown in FIG. 1 being worn about the waist of an individual.
Figure 7:
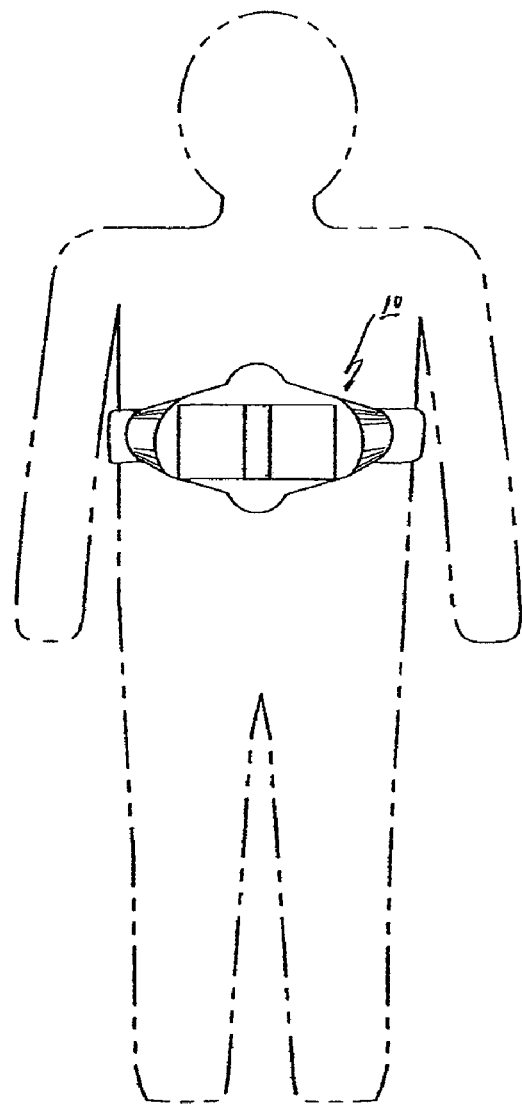
FIG. 7 is a view of the same garment shown in FIG. 1 being worn generally around the chest area of the individual.

As shown in FIGS. 6 and 7, the belt can be fastened about an individual's torso in different locations. FIG. 6 illustrates the garment 10 secured about the individual's waist and FIG. 7 shows the garment 10 secured generally about the individual's chest. It should be noted that FIGS. 6 and 7 are rear elevational views, actually depicting in phantom representation the back region of the individual.

The garment 10 is employed in the following manner:

The garment is placed about the torso of an individual in a desired location, e.g., the waist region or chest region, and the first strap portions 32 and 34 are secured tightly about the individual's torso through the cooperating Velcro fasteners 36, 38. It should be noted that, prior to securing the Velcro fasteners together the front strap portions 32 and 34 can be stretched tightly about the torso as a result of the attachment of the strap members to elastic sections 40 and 42.

When the garment 10 is placed about the torso of an individual, such as in the manner illustrated in FIGS. 6 and 7, and the individual is sleeping, he or she initially can be comfortably positioned in a prone position, on his or her stomach, or in a lateral position on his/her side. If the individual is in a lateral position the garment 10 is designed to assist in maintaining the individual in that position by the engagement of one of the side surfaces 14 or 16 (or one of the side edges 18 and 20 thereof) with the mattress or other sleeping surface. The particular side surface or edge that engages the mattress or other sleeping surface depends upon the specific side on which the individual is sleeping.

One of the significant benefits of this invention is that it aids in maintaining/supporting a sleeping person in a lateral position on his or her side. Although other devices have included structures for assisting in maintaining an individual in a lateral position while sleeping (e.g., see U.S. Pat. No. 6,926,008) applicant's device provides this function with a unique, position control member 12 that also provides a second, very important benefit. Specifically, the elongate positioning rib or abutment 26 extending outward from outer surface segments 22*a*, 22*b* is designed to engage the mattress or other sleeping surface in the event that an individual overrides one of the side surfaces 14 or 16 or side edges 18, 20 and moves into a supine position. When this occurs the positioning rib 26, although partially compressed when the position control member 12 is formed of a compressible material, provides a force that is transmitted to the wearer's back, thereby either waking up the wearer, or causing the wearer to seek a more comfortable position, e.g., either a prone or lateral position. Moreover, by maintaining a sleeping individual in a lateral or prone position, snoring tends to be minimized, or even eliminated.

In summary, the single, elongate position control member 12 provides the dual functions of assisting in maintaining an individual on his or her side (i.e., in a lateral position), to thereby avoid problems with sleep apnea, and also, in the event the individual does roll into a supine position, to provide a force against the individual's back that either will awake the individual or force the individual to simply return to either a lateral or prone sleeping position.

It should be understood that the elongate position control member 12 can be included as part of the garment 10 in various different ways. First, it can be formed as a separate member that is secured to the garment through cooperating fasteners attached to the inner surface 24 of the member 12 and the outer surface of the back panel 44. Alternatively, the back panel 44 can be provided with a pocket or pouch (or can actually be a pocket or pouch), e.g., made of nylon or other suitable material, secured thereto, into which the position control member 12 can be inserted and retained. In this regard, the inner surface of the pocket or pouch can be formed of a friction-containing material, such as a soft nylon to help retain the position control member 12 therein. Still further, the back panel 44 and the elongate position control member 12 can be formed as a unitary structure. The specific manner of securing the position control member 12 to the garment 10 is not considered to be a limitation on the broadest aspects of this invention.

Although the preferred embodiment of this invention includes the garment in the form of the belt or strap member illustrated herein, it should be understood that this belt member can include a variety of different structures, and is not limited to the particular structure illustrated in FIG. 1. For example, the belt member may be designed without any elastic section in it, and also with alternative types of fastening means. In addition, as noted above, the rear panel can actually be in the form of a pouch or pocket for retaining the position control member 12 therein.

Moreover, as noted earlier, the garment 10 maybe in the form of structures other than belts, such as jackets, shirts, straps, etc. Although FIG. 1 illustrates the most preferred construction for the garment 10, in accordance with the broadest aspects of this invention, the garment can include many different types of structures.

Although the most preferred embodiment of this invention has a raised, elongate positioning rib 26 extending outwardly from outer surface segments 22a, 22b, of the elongate position control member 12, it is within the broadest scope of this invention to eliminate the raised positioning rib 26, and simply provide the outer surface 22 as a continuous, generally planar surface. Although this is not considered to be the most preferred structure, it is believe that if an individual does roll into a supine position onto his or her back, the fact that the position control member 12 does extend outwardly from the rear surface of the belt 10 will cause that member to supply sufficient localized force to the wearer's back to either wake the individual up or force the individual to return to a prone or lateral position, possibly even without the inclusion of a vertically raised positioning rib 26 or other raised positioning abutment. Regardless of the specific structure of the position control member 12, it is significant to note that the preferred constructions are of a relatively simple, unitary structure.

It also should be noted that the garment 10, or at least the position control member 12, most likely will be provided in different sizes to accommodate individuals of varying sizes. Most likely, the garment will be offered in at least three sizes, e.g., small, medium and large. It may very well be desirable also to offer additional sizes, such as an extra large size.

In a representative, non-limiting example, the position control member can have an outer transverse dimension of 10 inches between outer edges 18 and 20, a transverse inner dimension of 8 inches between inner edges of the side surfaces 14 and 16, a depth dimension between the outer surface segments 22a, 22b and the inner surface 24 of approximately 3 inches, a depth dimension between the inner surface 24 and the apex of the raised positioning rib 26 of about 5 inches and a height, between upper and lower surfaces 28 and 30 of approximately 4 inches.

While the invention has been described in detail and with reference to specific embodiments and examples thereof, it will be apparent to one skilled in the art that various changes and modifications can be made therein without departing from the spirit and scope thereof.

What is claimed is:

1. A garment for the treatment of sleep apnea and/or snoring, to be worn by an individual afflicted with sleep apnea and/or snoring and preventing said individual from sleeping in a supine position, said garment including an elongate, position control member at the rear of the garment and extending outwardly therefrom, said position control member being a continuous member having transversely spaced-apart side surfaces, said side surfaces being joined to an outer surface of said member at elongate side edges, said position control member including a positioning rib extending outwardly from said outer surface.

2. The garment of claim 1, wherein the garment is selected from the group consisting of: belts, straps, shirts and vests.

3. The garment of claim 1, wherein the garment is at least partially formed of an elastic material.

4. The garment of claim 1, wherein the position control member is formed of a compressible material.

5. The garment of claim 1, wherein the positioning rib is generally vertically elongate, and positioned approximately midway between the side edges.

6. The garment of claim 5, wherein the geometry of the positioning rib is hemispherical.

7. The garment of claim 5, wherein the positioning rib is a unitary part of the position control member.

8. The garment of claim 1, said garment being a belt that is fastenable about the torso of the individual, said belt being at least partially formed of an elastic material which permits inspiratory chest excursion.

9. The garment of claim 1, said garment being a belt that is fastenable about the chest of the individual.

\* \* \* \* \*